United States Patent [19]

Meier et al.

[11] Patent Number: 5,416,234
[45] Date of Patent: May 16, 1995

[54] PROCESS FOR THE PREPARATION OF 3'-AMINOPROPYL 2-SULFATOETHYL SULFONE

[75] Inventors: Michael Meier; Heinrich Angenendt, both of Frankfurt am Main; Georg Grötsch, Hofheim am Taunus, all of Germany

[73] Assignee: Hoechst Aktiengesellschaft, Frankfurt, Germany

[21] Appl. No.: 108,569
[22] PCT Filed: Feb. 19, 1992
[86] PCT No.: PCT/EP92/00349
 § 371 Date: Aug. 25, 1993
 § 102(e) Date: Aug. 25, 1993
[87] PCT Pub. No.: WO92/15559
 PCT Pub. Date: Sep. 17, 1992

[30] Foreign Application Priority Data

Feb. 27, 1991 [DE] Germany .................. 41 06 106.3

[51] Int. Cl.⁶ ............................................ C07C 305/04
[52] U.S. Cl. .................................................... 558/29
[58] Field of Search .......................................... 558/29

[56] References Cited

U.S. PATENT DOCUMENTS 5,281,740  1/1994  Meier et al. ................ 558/29

Primary Examiner—Nicky Chan
Attorney, Agent, or Firm—Connolly & Hutz

[57] ABSTRACT

Process for the preparation of 3'-aminopropyl 2-sulfatoethyl sulfone in high yield, which comprises reacting allylamine with mercaptoethanol in aqueous sulfuric acid in a one-pot process at temperatures from about 25° C. to the boiling point of the reaction mixture in the presence of free-radical initiators which are soluble in the reaction medium, oxidizing the reaction mixture thus obtained with hydrogen peroxide in the presence of catalytic amounts of a compound of a transition metal of the periodic table of elements as oxidation catalyst to give 3'-aminopropyl 2-hydroxyethyl sulfone hemisulfate, adding further sulfuric acid until the total amount of sulfuric acid in the mixture is at least 1 mol, relative to the allylamine used, and esterifying the 3'-aminopropyl 2-hydroxyethyl sulfone hemisulfate obtained after oxidation by evaporation to dryness or with sulfuric acid or oleum or chlorosulfonic acid in solution.

12 Claims, No Drawings

PROCESS FOR THE PREPARATION OF 3'-AMINOPROPYL 2-SULFATOETHYL SULFONE

This application is a 371 of PCT/EP92/00349 filed Feb. 19, 1992.

The invention relates to an improved process for the preparation of 3'-aminopropyl 2-sulfatoethyl sulfone by an addition reaction of mercaptoethanol with allylamine in aqueous sulfuric acid in the presence of free-radical initiators, oxidation of the reaction mixture thus obtained with hydrogen peroxide in the presence of catalytic amounts of transition metal compounds and esterification with sulfuric acid or oleum or chlorosulfonic acid, using free-radical initiators which are soluble in the reaction medium.

3'-Aminopropyl 2-sulfatoethyl sulfone is an important precursor for the preparation of reactive dyes (EP 0141776).

The preparation of 3'-aminopropyl 2-sulfatoethyl sulfone is described in European Patent 0,518,889, in which allylamine is reacted with mercaptoethanol in aqueous sulfuric acid in a one-pot process at temperatures from about 50° C. to the boiling point of the reaction mixture in the presence of free-radical initiators, the reaction mixture formed is oxidized with hydrogen peroxide in the presence of catalytic amounts of a compound of a transition metal of the periodic table of elements at temperatures from about 70° to about 100° C., further sulfuric acid is added until the total amount of sulfuric acid in the mixture is at least 1 mol, relative to the allylamine used, and the 3'-aminopropyl 2-hydroxyethyl sulfone hemisulfate is esterified by evaporation to dryness.

The reaction times of the free-radical addition reaction of mercaptoethanol with allylamine are in this reaction between 35 and 45 hours.

Surprisingly, it has now been found that the reaction time of the process described can be considerably shortened and high yields can be obtained by using free-radical initiators, preferably 2,2'-azobis[2-(2-imidazolin-2-yl)propane] or its dihydrochloride or 2,2'-azobis(2-amidinopropane) dihydrochloride, which are soluble in the reaction medium and carrying out the reaction of allylamine with mercaptoethanol in aqueous sulfuric acid at about 25° C. to the boiling point of the reaction mixture, preferably at the temperature at which the free-radical initiator has a half-life of about 1 to about 5 hours, followed by oxidation and esterification.

Accordingly, the invention relates to an improved process for the preparation of 3'-aminopropyl 2-sulfatoethyl sulfone in high yields and in a relatively short reaction time by reaction of allylamine with mercaptoethanol in aqueous sulfuric acid in a one-pot process at temperatures from about 25° C. to the boiling point of the reaction mixture in the presence of free-radical initiators which are soluble in the reaction medium, oxidation of the reaction mixture thus obtained with hydrogen peroxide in the presence of catalytic amounts of a compound of a transition metal of the periodic table of elements as oxidation catalyst to give 3'-aminopropyl 2-hydroxyethyl sulfone hemisulfate, addition of further sulfuric acid until the total amount of sulfuric acid in the mixture is at least 1 mol, relative to the allylamine used, and esterification of the 3'-aminopropyl 2-hydroxyethyl sulfone hemisulfate obtained after oxidation by evaporation to dryness or with sulfuric acid or oleum or chlorosulfonic acid in solution.

It is advantageous to initially introduce 1 mol of allylamine in aqueous sulfuric acid at a temperature at which the free-radical initiator has a half-life of about 1 to about 5 h, and to meter in 0.9 to about 1.5 mol, preferably about 0.95 to about 1.05 mol, of mercaptoethanol, in which 0.1 to about 5 g, preferably about 0.5 to about 1.5 g, of free-radical initiator are dissolved per mole of mercaptoethanol. It is also possible to initially introduce mercaptoethanol, in which 0.1 to about 5 g, preferably about 0.5 to about 1.5 g, of free-radical initiator are dissolved per mole of mercaptoethanol, and to meter in 1 mol of allylamine in aqueous sulfuric acid at a temperature at which the free-radical initiator has a half-life of about 1 to 5 h. However, the procedure can also be such that 1 mol of allylamine in aqueous sulfuric acid and about 0.1 to about 1.0 mol of mercaptoethanol are initially introduced at a temperature at which the free-radical initiator has a half-life of about 1 to 5 h, and 0.1 to 5 g, preferably 0.5 to 1.5 g, of free-radical initiator per mole of mercaptoethanol are metered in dissolved in the remaining mercaptoethanol or in water. However, it is also possible to initially introduce all components together, although this is problematical when carried out on an industrial scale, due to the heat of reaction given off.

The preferred temperature range for 2,2'-azobis-[2-(2-imidazolin-2-yl)propane] or its dihydrochloride is about 45° to about 65° C. and for 2,2'-azobis(2-amidinopropane) dihydrochloride about 55° to 75° C.

Compounds which serve as compounds of a transition metal of the periodic table of elements are preferably those of tungsten or vanadium as oxidation catalyst, such as, for example, $Na_2WO_4 \times 2H_2O$ or $NaVO_3$.

The process according to the invention is advantageously carried out at atmospheric pressure; however, the process can also be carried out at elevated or reduced pressure. Compared with the process described in German Patent Application P 40 07 049.2, the use of free-radical initiators which are soluble in the reaction mixture, such as, for example, 2,2'-azobis[2-(2-imidazolin-2-yl)propane] or its dihydrochloride or 2,2'-azobis(2-amidinopropane) dihydrochloride, shortens the reaction time of the reaction of allylamine with mercaptoethanol in aqueous sulfuric acid to about 3 to 8 h compared with 35 to 45 h. The significantly shortened reaction times lead to a strong increase in the space-time yields, which makes the process particularly economical.

The examples which follow illustrate the invention in more detail without limiting it.

EXAMPLE 1

100.0 g of ice and 61.3 g (0.6 mol) of 96% sulfuric acid are initially introduced into to a 1 l four-neck flask equipped with stirrer, dropping funnel, thermometer and reflux condenser. 57.1 g (1.0 mol) of allylamine are run into this mixture. 78.1 g (1.0 mol) of mercaptoethanol to which 1 g of 2,2'-azobis[2-(2-imidazolin-2-yl propane] dihydrochloride has been added are then metered into this mixture over a period of 1 h. Stirring at 55° to 60° C. is then continued for a total of 3 h. After the reaction is complete, 0.05 g of sodium tungstate dihydrate is added to the solution and 113.3 g (1.0 mol) of 30% hydrogen peroxide are metered in at 80° C. over a period of 1 hour. To maintain the temperature of 80° C., cooling with ice water is necessary. Another 113.3 g (1.0 mol) of 30% hydrogen peroxide are then metered in at 80° C. After metering-in is complete, stirring at 80° C.

is continued for 1 h. To esterify the hydroxyethyl sulfone formed, 46.0 g (0.45 mol) of 96% sulfuric acid are added. At a temperature of 80° C./200 mbar, the reaction mixture is added dropwise to a laboratory kneader. The temperature is then slowly raised to 150° C./1 mbar, and the mixture is finally evaporated to dryness. This gives 253.9 g of 3'-aminopropyl 2-sulfatoethyl sulfone of purity 93.2%. The yield is 95.4% of theory.

Melting point: 235°–240° C. (decomposition) $^1$H NMR ([D$_6$]DMSO): $\delta$=2.0 (q, J=7 Hz; CH$_2$CH$_2$CH$_2$CH$_2$, 2H), 2.9 (m; C$\underline{H}_2$NH$_3$+; 2H), 3.2 (m; SO$_2$C$\underline{H}_2$CH$_2$; 2H), 3.4 (t, J=7 Hz; CH$_2$CH$_2$SO$_2$), 4.1 (t, J=7 Hz; CH$_2$OSO−; 2H ), 7.7 (broad; NH$_3$+; 3H). IR(UBr): 3160,2990,2935,1320,1290,1205,1060 cm$^{-1}$.

EXAMPLE 2

100.0 g of ice and 61.3 g (0.6 mol) of 96% sulfuric acid are initially introduced into to a 1 l four-neck flask equipped with stirrer, dropping funnel, thermometer and reflux condenser. 57.1 g (1.0 mol) of allylamine are then run into this mixture. 78.1 g (1.0 mol) of mercaptoethanol to which 1 g of 2,2'-azobis(2-amidinopropane) dihydrochloride has been added are then metered into this mixture at about 70° C. Stirring at this temperature is then continued for 4 hours. After the reaction is complete, 0.025 g of sodium tungstate dihydrate is added to the solution at 80° C. and 97.1 g (1.0 mol) of 35% hydrogen peroxide are metered in over a period of 1 hour. To maintain the temperature of 80° C., cooling with ice water is carried out. Another 97.1 g (1.0 mol) of 35% hydrogen peroxide are then metered in at 80° C. After metering-in is complete, stirring at 80° C. is continued for 1 hour. To esterify the hydroxyethyl sulfone formed, 46.0 g (0.45 mol) of 96% sulfuric acid are added. At a temperature of 80° C./200 mbar, the reaction mixture is added dropwise to a laboratory kneader and the temperature is then slowly raised to 150° C./1 mbar, and the mixture is evaporated to dryness. This gives 251.5 g of 3'-aminopropyl 2-sulfatoethyl sulfone of purity 95.3%. Accordingly, the yield is 96.9% of theory.

Melting point: 235°–240° C. (decomposition)

The spectroscopic data are identical to those given in Example 1.

EXAMPLE 3

100.0 g of ice and 61.3 g (0.6 mol) of 96% sulfuric acid are initially introduced into a 1 l four-neck flask equipped with stirrer, dropping funnel, thermometer and reflux condenser. 57.1 g (1.0 mol) of allylamine are then run into this mixture. 39.05 g (0.5 mol) of mercaptoethanol are metered into this mixture, which is then heated to 50° C. 39.05 g (0.5 mol) of mercaptoethanol to which 1 g of 2,2'-azobis[2-(2-imidazolin-2-yl)propane] dihydrochloride has been added are metered into this reaction mixture over a period of 30 minutes. Stirring at 60° C. is then continued for a total of 3 hours. The further reaction is as described in Example 1. This gives 250.3 g of 3'-aminopropyl 2-sulfatoethyl sulfone of purity 93.8%. Accordingly, the yield is 94.9% of theory.

Melting point: 235°–240° C. (decomposition).

The spectroscopic data are identical to those given in Example 1.

EXAMPLE 4

100.0 g of ice and 61.3 g (0.6 mol) of 96% sulfuric acid are initially introduced into a 1 l four-neck flask equipped with stirrer, dropping funnel, thermometer and reflux condenser. 57.1 g (1.0 mol) of allylamine are run into this mixture. 78.1 g (1.0 mol) of mercaptoethanol to which 1 g of 2,2'-azobis[2-(2-imidazolin-2-yl)propane] dihydrochloride has been added are then metered into this mixture at 55° C. over a period of 1 hour. Stirring at 55 to 60° C. is then continued for a total of 3 hours. After the reaction is complete, 0.05 g of sodium tungstate dihydrate is added to the solution and 113.3 g (1.0 mol) of 30% hydrogen peroxide are metered in at 80° C. over a period of 1 hour. To maintain the temperature of 80° C., cooling with ice water is necessary. Another 113.3 g (1.0 mol) of 30% hydrogen peroxide are then metered in at 80° C.

The oxidation solution is evaporated in vacuo until it is only just stirrable. 47.6 g of 100% sulfuric acid and 199.4 g of 65% oleum are then added. After additional stirring up to 120° C. for 2 hours, the mixture is cooled to 25° C. and poured into a cold ethanol/water mixture. The crystals formed are filtered off with suction, thoroughly washed and dried. The yield is 235.9 g (95.4% of theory) of 3'-aminopropyl 2-sulfatoethyl sulfone (content: 95% by weight).

Melting point: 235°–240° C. (decomposition).

The spectroscopic data are identical to those given in Example 1.

EXAMPLE 5

100.0 g of ice and 61.3 g (0.6 mol) of 96% sulfuric acid are initially introduced into to a 1 l four-neck flask equipped with stirrer, dropping funnel, thermometer and reflux condenser. 57.1 g (1.0 mol) of allylamine are run into this mixture. 78.1 g (1.0 mol) of mercaptoethanol to which 1 g of 2,2'-azobis[2-(2-imidazolin-2-yl)propane]dihydrochloride has been added are then metered into this mixture at 55° C. over a period of 1 hour. Stirring at 55° to 60° C. is then continued for a total of 3 hours. After the reaction is complete, 0.05 g of sodium tungstate dihydrate is added to the solution and 113.3 g (1.0 mol) of 30% hydrogen peroxide are metered in at 80° C. over a period of 1 hour. To maintain the temperature of 80° C., cooling with ice water is necessary. Another 113.3 g (1.0 mol) of 30% hydrogen peroxide are then metered in at 80° C. After metering-in is complete, stirring at 80° C. is continued for 1 hour.

The oxidation solution is evaporated in vacuo until it is only Just stirrable. 169.5 g of 100% sulfuric acid and 133.7 g of chlorosulfonic acid are then added at 80° C. The mixture is then cooled to 25° C. and poured into a cold ethanol/water mixture. The crystals formed are filtered off with suction and washed. Drying gives 225.4 g (91.1% of theory) of 3'-aminopropyl 2-sulfatoethyl sulfone (content: 95% by weight).

Melting point: 235°–240° C. (decomposition).

The spectroscopic data are identical to those given in Example 1.

EXAMPLE 6

100.0 g of ice and 61.3 g (0.6 mol) of 96% sulfuric acid are initially introduced into to a 1 l four-neck flask equipped with stirrer, dropping funnel, thermometer and reflux condenser. 57.1 g (1.0 mol) of allylamine are run into this mixture. 78.1 g (1.0 mol) of mercaptoethanol to which 1 g of 2,2'-azobis[2-(2-imidazolin-2-yl)propane] dihydrochloride has been added are then metered into this mixture at 55° C. over a period of 1 hour. Stirring at 55° to 60° C. is then continued for a total of 3 hours. After the reaction is complete, 0.05 g of sodium tungstate dihydrate is added to the solution and 226.6 g (2.0 mol) of 30% hydrogen peroxide are metered in at 100° C. over a period of 1 hour. After metering-in is complete, stirring at 100° C. is continued for 1 hour.

The oxidation solution is evaporated in vacuo until it is only just stirrable. 169.5 g of 100% sulfuric acid and 133.7 g of chlorosulfonic acid are then added at 80° C. The mixture is then cooled to 25° C. and poured into a cold ethanol/water mixture. The crystals formed are filtered off with suction and washed. Drying gives 225.3 g (91.1% of theory) of 3'-aminopropyl 2-sulfatoethyl sulfone (content: 96.8% by weight).

Melting point: 235°–240° C. (decomposition).

The spectroscopic data are identical to those given in Example 1.

We claim:

1. A process for the preparation of 3'-aminopropyl 2-sulfatoethyl sulfone in high yield, which comprises reacting allylamine with mercaptoethanol in aqueous sulfuric acid in a one-pot process at temperatures from about 25° C. to the boiling point of the reaction mixture in the presence of 2,2'-azobis[2-(2-imidazolin-2-yl)propane, 2,2'-azobis[2-(2-imidazolin-2-yl)propane] dihydrochloride or 2,2'-azobis(2-amidinopropane) dihydrochloride or mixtures thereof, as a free-radical initiator, oxidizing the reaction mixture thus obtained with hydrogen peroxide in the presence of catalytic amounts of tungsten or vanadium as oxidation catalyst to give 3'-aminopropyl 2-hydroxyethyl sulfone hemisulfate, adding further sulfuric acid until the total amount of sulfuric acid in the mixture is at least 1 mol, relative to the allylamine used, and esterifying the 3'-aminopropyl 2-hydroxyethyl sulfone hemisulfate obtained after oxidation by evaporation to dryness or with sulfuric acid or oleum or chlorosulfonic acid in solution.

2. The process as claimed in claim 1, wherein the reaction of allylamine with mercaptoethanol is carried out in aqueous sulfuric acid at a temperature at which the free-radical initiator has a half-life of about 1 to about 5 hours.

3. The process as claimed in claim 1, wherein when 2,2'-azobis[2-(2-imidazolin-2-yl)propane] or its dihydrochloride is used, the reaction of allylamine with mercaptoethanol is carried out in aqueous sulfuric acid at about 45° to about 65° C.

4. The process as claimed in claim 1, wherein when 2,2'-azobis(2-amidinopropane) dihydrochloride is used, the reaction of allylamine in aqueous sulfuric acid with mercaptoethanol is carried out at about 55° to about 75° C.

5. The process as claimed in claim 1, wherein the oxidation is carried out in the presence of a compound of tungsten or vanadium as oxidation catalyst.

6. The process as claimed in claim 1, wherein the oxidation is carried out in the presence of $Na_2WO_4 \times 2H_2O$ as oxidation catalyst.

7. The process as claimed in claim 1, wherein the oxidation is carried out in the presence of $NaVO_3$ as oxidation catalyst.

8. The process as claimed in claim 1, wherein the reaction is carried out at atmospheric pressure.

9. The process as claimed in claim 1, wherein the reaction is carried out at reduced pressure.

10. The process as claimed in claim 1, wherein the reaction is carried out at superatmospheric pressure.

11. The process as claimed in claim 1, wherein the allylamine is reacted with mercaptoethanol in aqueous sulfuric acid for 3 to 8 hours.

12. The process as claimed in claim 11, wherein the allylamine is reacted with mercaptoethanol in aqueous sulfuric acid for about 3 to 4 hours.

* * * * *